United States Patent [19]

Lawrence et al.

[11] 4,131,370
[45] Dec. 26, 1978

[54] MICRO STIRRER

[75] Inventors: Noel L. W. Lawrence; Surinder S. Latti, both of London, Canada

[73] Assignee: Temtron Electronics Ltd., London, Canada

[21] Appl. No.: 783,872

[22] Filed: Apr. 1, 1977

[30] Foreign Application Priority Data

Mar. 17, 1977 [CA] Canada .................................. 274181

[51] Int. Cl.² ............................................. B01F 13/08
[52] U.S. Cl. ................................................... 366/273
[58] Field of Search ................ 259/DIG. 46, 64, 111; 318/175, 207 E, 696; 310/103, 156; 356/180, 181, 229; 366/273, 274

[56] References Cited

U.S. PATENT DOCUMENTS

| 2,639,411 | 5/1953 | Schafer | 318/207 E X |
|---|---|---|---|
| 2,641,452 | 6/1953 | Wagner | 366/273 |
| 2,875,261 | 2/1959 | Hanff | 259/DIG. 46 |
| 2,951,689 | 9/1960 | Asp et al. | 259/DIG. 46 |
| 2,972,784 | 2/1961 | Shonka et al. | 259/DIG. 46 |
| 2,999,673 | 9/1961 | Kessler | 366/273 X |
| 3,344,325 | 9/1967 | Sklaroff | 318/696 |
| 3,784,170 | 1/1974 | Petersen et al. | 259/DIG. 46 |
| 3,997,272 | 12/1976 | George | 366/274 X |

Primary Examiner—Philip R. Coe
Attorney, Agent, or Firm—Lavine & Jackson

[57] ABSTRACT

A small magnet for stirring a cuvette is disclosed and the means by which the small magnet is rotated within the cuvette without any mechanical connection. Thus solutions within the cuvette may be measured and monitored, if necessary, in the total absence of daylight which reduces the impact of noise on sensors commonly used when spectrophotometric and spectroflourometric studies of solutions within the cuvette are performed.

5 Claims, 6 Drawing Figures

U.S. Patent  Dec. 26, 1978  Sheet 1 of 2  4,131,370
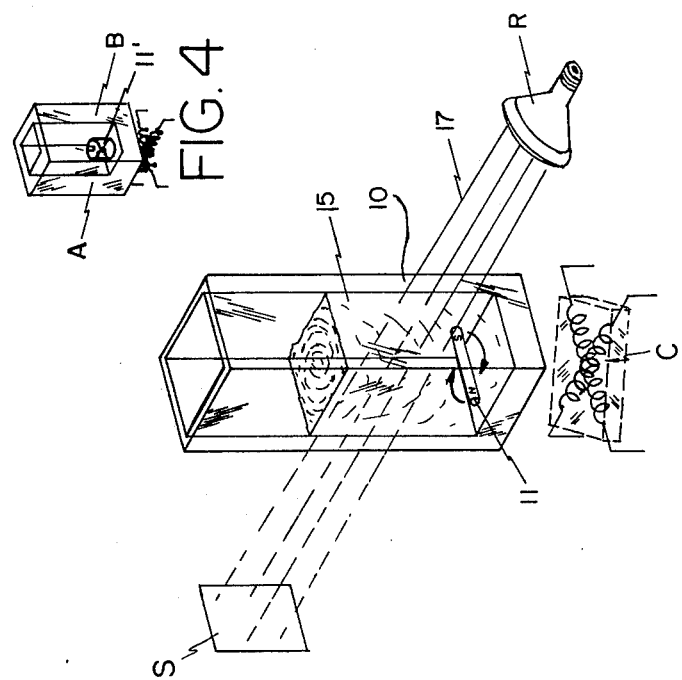
FIG. 4
FIG. 2
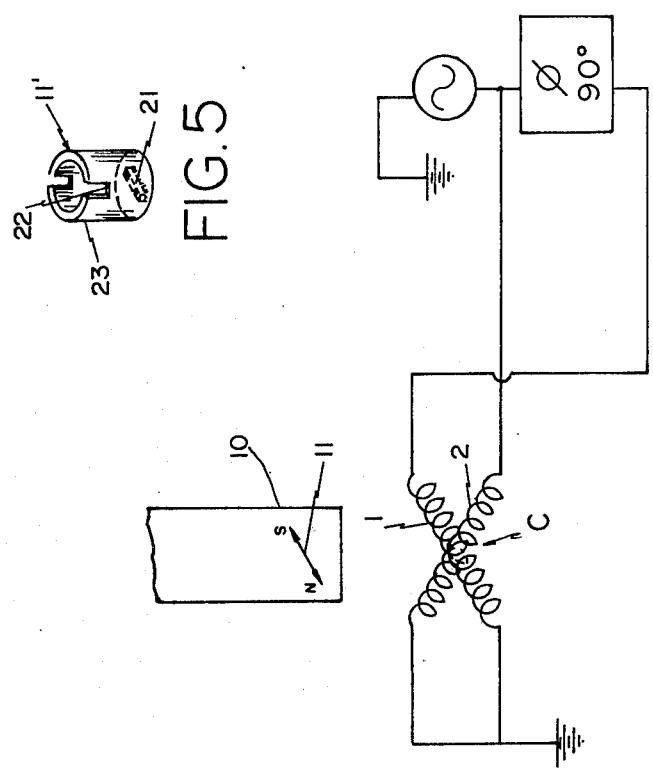
FIG. 5
FIG. 1

MICRO STIRRER

This invention relates to an apparatus for stirring micro volumes of solutions whose properties are to be analyzed during the stirring by various means.

In particular the invention relates to a micro stirrer designed to enable users of spectrophotometers and spectroflourometers to conduct analysis as for example, photosynthesis analysis on flourescent materials or kinetic studies of enzymes accurately and efficiently under normal conditions while inducing the liquid into agitation during the spectrophotometric and spectroflourometric studies.

It is common when these studies are conducted to place the sample material inside a cuvette and to place the cuvette between a source of radiation and a sensor whereby measurements are taken. In some applications, stirring must take place in total darkness in order to eliminate or reduce the ambient noise level on the sensor. This is difficult to do unless the sample solution within the cuvette can be automatically or controllably stirred.

It has been conceived therefore to use a small magnet as a stirring instrument within a cuvette. Particularly to cause a small magnet to be rotated by means of a moving magnetic field and to thereby cause the small magnet to spin within the cuvette and to agitate the solution therein. In one embodiment this may be accomplished by energizing two orthoginal electromagnetic coils, one with a sine wave and the other with a cosine wave. Alternatively, in another embodiment four coils may be placed in a common plane to form essentially a closed square each coil being a sequentially and periodically energized by electric energy in a square wave form to thereby create a magnetic field which rotates.

The invention therefore contemplates a micro stirrer for stirring a solution within a cuvette comprising:
(a) a longitudinal magnetic member placed within the cuvette adapted to freely move and to rotate therein in response to a rotating magnetic field; and,
(b) means for creating a rotating magnetic field which extends into the cuvette and to influence the magnetic member, whereby the magnetic member is moved into rotation in response to the rotating magnetic field and imparts by its motion, agitation to the contents of the cuvette.

In an alternative embodiment, the invention contemplates a plurality of cuvettes each containing a rotatable magnetic member each subject to his own rotating magnetic field for driving its magnetic member into rotation.

The invention will now be described by way of example and reference to the accompanying drawings in which:

FIG. 1 is a schematic diagram, illustrating an embodiment of the invention;

FIG. 2 is a perspective, diagrammatically illustrating, the mixing of a solution within the cuvette during its monitoring;

FIG. 4 is a perspective of an alternative cuvette;

FIG. 5 is a perspective of an alternative stirrer adapted for utilization with the cuvette of FIG. 4; and, FIG. 6 is an electrical schematic diagram of an alternative embodiment.

Figure 6:
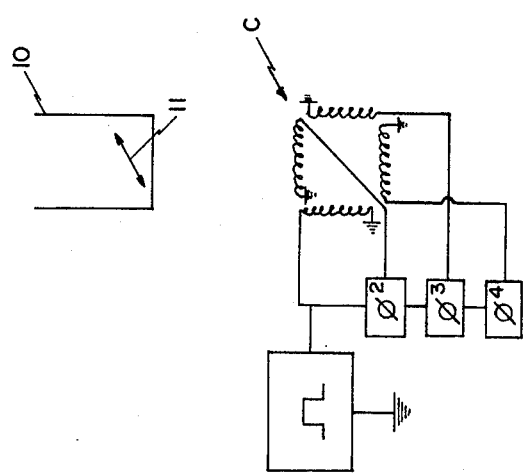

Referring now to FIG. 1, a cuvette 10 has within it a cylindrical permanent magnet 11 of about 8 millimeters long and 3 millimeters in diameter, preferably coated with an inert material such as TEFLON® and is adapted to move within the cuvette. The cuvette is placed over two electromagnetic coils C1 and C2, which are orthoginal to each other. The coils are preferably encapsulated as C into a polymetric material for instance, bakelite, plastic or the like, so as to give structural rigidity to the orthoginal coils. One end of each of the ends of the coils C1 and C2 is connected to ground while the other end of one coil is connected directly to a sine wave generator or oscillator, and the other to a phase shift network $\phi$ which shifts the phase of the output of a generator 90° and hence creates a cosine wave as output. Hence, the orthoginal coils C impart a rotating magnetic field which extends into the cuvette and impacts on the permanent magnet 11 there to drive it into circular motion. The magnet thus acts, because of its physical length and diameter, as the stirrer for the solution 15 within the cuvette.

Referring to FIG. 2, the cuvette 10 has within it a solution 15 and is placed to interrupt an appropriate stream 17 of radiation emanating from a radiator R and collected by a sensor S. Depending upon the type of radiator and sensor, different properties of the fluid can be measured for instance, its flourometric or photometric properties. Thus, the sensor could be a photomultiplier or other device and the radiator a light source, etc.

Those familiar with the art will appreciate that the oscillator and the phase shift network $\phi$ may be supplemented by outboard amplifiers (not shown) to increase the electric field and hence the amplitude of the rotative magnetic field generated by the coil network C. The coils C1 and C2 are wound preferably with #32 guage high grade copper wire, solvent insulated such that with a current of 500 ma., a ½ inch height of magnetic field is generated into the cuvette so that the magnetic bar stirrer 11 will be effectively influenced by the rotating magnetic field.

It should be appreciated in this sphere of scientific measurement (spectrophotometric and flourometric studies) cuvettes are small and range about one centimeter square in cross-section to hold about one milliliter of solution. Thus the magnetic rod must be short enough to clear the inside dimensions of the cuvette.

In some applications even a one milliliter cuvette is too large; 0.5 milliliter cuvettes are thus used. Referring to FIG. 4 and such a cuvette, the outside dimensions of the cuvette are the same as those of FIG. 2, namely one centimeter, but the inside is reduced by extending the thickness of the lateral walls A relative to the front and rear walls B. Thus the volume of the cuvette is reduced. The bar magnet 11 which also acted as the stirrer in the earlier described embodiments, is unsatisfactory since it is too large to freely spin within the smaller cuvette of FIG. 4. Thus referring to FIG. 5 a stirrer 11' includes a cylindrical member 23 with a permanent magnet 21 affixed to its floor. Appropriate grooves 22 are diametrically positioned in the upper lip of the cylinder 23. The grooves on spinning of the stirrer 11', cause turbulence to the solution and hence stirring of the liquid within the smaller cuvette of FIG. 4. The diameter of the cylinder member 23 is small enough to permit spinning in the cuvette of FIG. 4.

It has been found in certain studies that TEFLON ® is hygroscopic in relation to the materials or the solution to be monitored. Thus it is desirable to eliminate the TEFLON ®. The permanent magnet may be a stainless steel magnet.

Figure 3:
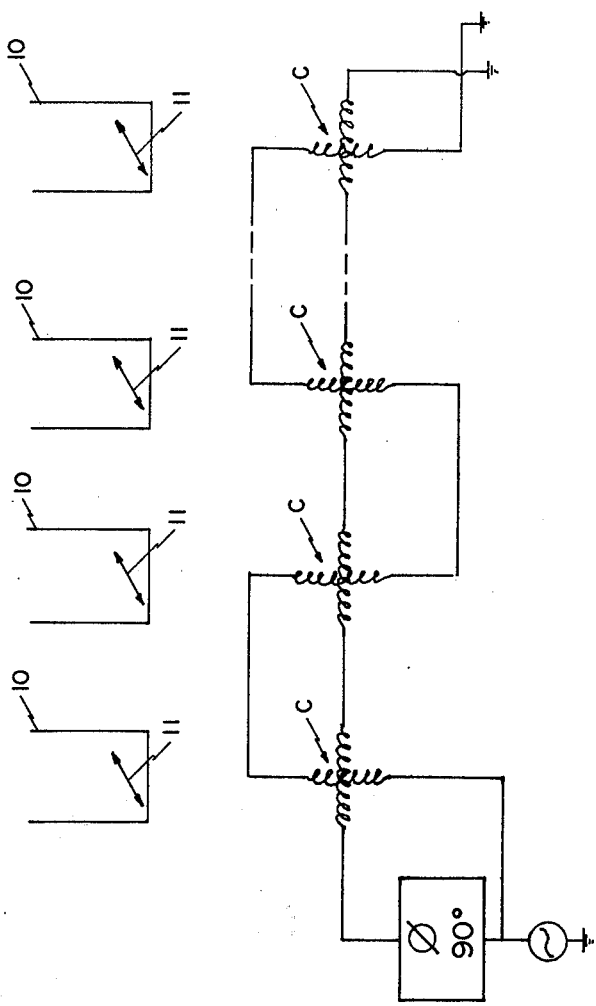
FIG. 3 is a diagrammatic representation of apparatus for stirring the solutions within a multitude of cuvettes simultaneously.

In another embodiment of the invention, a number of coils C may be placed in series (which reduces the impedance load on the oscillator and phase shift network) and thus a number of cuvettes may be simultaneously stirred, measured and monitored. Referring to FIG. 3 such an embodiment is disclosed. Thus one may use one of the cuvettes as the base point or 'standard' and the other cuvettes may house different solutions or mixtures which can be comparatively measured by conventional means in relation to the standard.

Referring to another alternative embodiment and to FIG. 6, a square wave generator with phase shift networks may be used to sequentially pulse four coils arranged to lie in the same plane but placed end to end to form a closed figure such as a square. A rotating magnetic field is created by the sequential pulsing of each of the coils.

Typically, frequencies in the range of 9–30 Hz can be used to achieve stirring.

EXPERIMENTAL USE

The stirrer was used in a series of experiments involving the interaction of mitochondrial membranes with a dye. The extent of the interaction is measured by the enhancement of fluorescence of the dye. The stirrer disclosed in FIGS. 1 and 2 permitted the measurement of not only the total fluorescence but more importantly, the rate of increase of fluorescence; something which to date has been impossible to achieve in fluorimeters typically presently found. Thus the researchers were able to make additions to the reaction cuvette through the lid of the reaction chamber without disturbing the light characteristics of the system and hence were able to monitor the early kinetics of the interaction.

The ability to continuously stir the solutions within the cuvette, maintains a uniform oxygen tension throughout the reaction cell which was not previously achieved.

It is thus possible now by employing the invention to continuously monitor a variety of other optical changes, e.g. spectral, turbidity etc., without interruption particularly in turbid structures containing mitochondria, microsomes and chloroplasts. Continuous stirring during measurements decreases the possibility of artifacts due to settling out of these particles. More importantly, the embodiments of the invention can be used without interference of the light sensing system which measure the solution.

The embodiments of the invention in which an exclusive property or privilege is claimed, are defined as follows:

1. A micro stirrer for stirring the solution within a cuvette comprising:
   (a) a longitudinal magnetic member freely mounted within the cuvette and adapted to rotate in response to a magnetic field;
   (b) four coils lying in the same plane each orthoginally placed relative to adjacent coils and said coils placed below the exterior of the cuvette; and,
   (c) means for energizing, sequentially, each of the said coils momentarily with a square wave form whereby a rotational magnetic field is created by the coils, a portion of the magnetic field extending upwardly into the cuvette to influence the magnetic member and to thereby impart rotation to the member in response to the magnetic field, the rotating member stirring the contents of the cuvette.

2. The stirrer as claimed in claim 1 wherein the magnetic member is coated with an inert non-magnetic material.

3. The stirrer as claimed in claim 1 wherein the magnetic member is stainless steel.

4. The stirrer as claimed in claim 1 wherein the magnetic member is a permanent magnet affixed to a member having a continuous cylindrical outer surface and positioned therein with its magnetic poles thereof diametric to the longitudinal axis of said cylindrical surface of said member, and means on the said member for causing turbulence to the solution as said member is rotated by the permanent magnet in response to the migrating magnet field.

5. A plurality of adjacent micro stirrers as claimed in claim 1 each micro stirrer stirring a separate and independent solution within its own individual cuvette and means including a source of energy and sensors therefore so that energy from the source extends through each cuvette to individual sensors and the solutions within the cuvettes as stirred can be individually monitored.

* * * * *